(12) United States Patent
Tweardy et al.

(10) Patent No.: US 8,356,604 B2
(45) Date of Patent: Jan. 22, 2013

(54) IMMOBILIZATION DEVICE

(75) Inventors: Lisa Tweardy, Moorestown, NJ (US); Jeff Nemeth, Chandler, AZ (US)

(73) Assignee: Ossur HF, Reykjavik (IS)

( * ) Notice: Subject to any disclaimer, the term of this patent is extended or adjusted under 35 U.S.C. 154(b) by 355 days.

(21) Appl. No.: 12/617,819

(22) Filed: Nov. 13, 2009
(Under 37 CFR 1.47)

(65) Prior Publication Data
US 2011/0114101 A1 May 19, 2011

(51) Int. Cl.
*A61F 5/37* (2006.01)
*A61F 5/00* (2006.01)
*A61B 19/00* (2006.01)
*A41D 27/26* (2006.01)

(52) U.S. Cl. ............ 128/870; 602/17; 602/18; 128/874; 128/869; 2/462

(58) Field of Classification Search .......... 602/5, 17–20, 602/36–37, 32; 128/870, 874, 869, 846; 2/462, 467, 102, 126, 113; 606/286, 289
See application file for complete search history.

(56) References Cited

U.S. PATENT DOCUMENTS

| | | | |
|---|---|---|---|
| 2,166,229 A | 1/1937 | Anderson |
| 2,474,200 A | 6/1949 | McBee |
| 2,706,982 A | 4/1955 | Hale et al. |
| 2,828,737 A | 4/1958 | Hale |
| D186,642 S | 11/1959 | Hale |
| 2,973,030 A | 2/1961 | Matthewson |
| 3,601,123 A | 8/1971 | McFarland |
| 3,605,736 A | 9/1971 | D'Amico |
| 3,724,452 A | 4/1973 | Nitschke |
| 3,795,243 A | 3/1974 | Miller |
| 3,799,156 A | 3/1974 | Gurkin |
| 3,827,429 A | 8/1974 | Heikes |
| 3,945,376 A | 3/1976 | Kuehnegger |
| D245,537 S | 8/1977 | Gurgiolo |
| 4,194,501 A | 3/1980 | Watt |
| 4,383,523 A | 5/1983 | Schurman |
| D277,236 S | 1/1985 | Gregory |
| 4,502,471 A | 3/1985 | Owens |
| 4,515,153 A | 5/1985 | Calabrese |
| 4,520,801 A | 6/1985 | Lerman |
| 4,539,979 A | 9/1985 | Bremer |
| 4,541,421 A | 9/1985 | Iversen et al. |
| D286,073 S | 10/1986 | Russell |
| 4,620,530 A | 11/1986 | Lanier et al. |
| 4,628,913 A | 12/1986 | Lerman |
| 4,632,099 A | 12/1986 | Mollo |
| 4,677,969 A | 7/1987 | Calabrese |
| 4,732,144 A | 3/1988 | Cunanan |
| D296,595 S | 7/1988 | Flosi et al. |
| 4,776,327 A | 10/1988 | Russell |
| 4,807,605 A | 2/1989 | Mattingly |
| D302,308 S | 7/1989 | Russell |

(Continued)

*Primary Examiner* — Michael Brown
*Assistant Examiner* — George N Phillips
(74) *Attorney, Agent, or Firm* — Bacon & Thomas, PLLC

(57) ABSTRACT

An immobilization device including an anterior component including a two-dimensional shaped section contoured to a shape of the human chest and an anterior outwardly bowed area relative to the two-dimensional shaped anterior section generally corresponding to the sternum of the wearer. The device also includes a posterior component including a two-dimensional shaped section contoured to a shape of the human back and a posterior outwardly bowed area relative to the two-dimensional shaped section corresponding to the spinal column of the wearer, with elongate cushion elements connected to and extending within a width of the posterior outwardly bowed area. A strapping system connects both the anterior and posterior components to one another.

6 Claims, 8 Drawing Sheets

U.S. PATENT DOCUMENTS

| | | |
|---|---|---|
| 4,913,135 A | 4/1990 | Mattingly |
| D311,608 S | 10/1990 | Harding |
| 5,121,741 A * | 6/1992 | Bremer et al. .................. 602/18 |
| 5,171,296 A | 12/1992 | Herman |
| D340,784 S | 10/1993 | Clayton |
| 5,261,873 A * | 11/1993 | Bremer et al. .................. 602/32 |
| 5,531,669 A | 7/1996 | Varnau |
| 5,564,788 A | 10/1996 | Warhaftig |
| 5,865,780 A | 2/1999 | Tuite |
| 5,964,722 A | 10/1999 | Goralnik et al. |
| 6,315,746 B1 | 11/2001 | Garth et al. |
| 6,663,630 B2 | 12/2003 | Farley et al. |
| 6,722,077 B2 * | 4/2004 | Heiges ................................ 43/3 |
| D492,819 S | 7/2004 | Beland |
| 6,921,376 B2 | 7/2005 | Tweardy et al. |
| D556,383 S | 11/2007 | Petzl |
| D597,708 S | 8/2009 | Basenberg, Jr. et al. |
| D600,860 S | 9/2009 | Durham |
| 7,987,523 B2 * | 8/2011 | Cole et al. ......................... 2/102 |
| 2008/0250552 A1 * | 10/2008 | Durham ............................ 2/456 |
| 2009/0209894 A1 * | 8/2009 | McAllister ...................... 602/19 |
| 2010/0298749 A1 | 11/2010 | Garth et al. |

\* cited by examiner

IMMOBILIZATION DEVICE

FIELD OF THE INVENTION

The present invention relates to an immobilization device for use by wearers having cervical or spinal injuries. Specifically, the immobilization device functions to fully or partially immobilize the head and neck of the wearer by way of vest components for supporting and transferring loads from halo support rods which support a halo about a wearer's head.

BACKGROUND

Immobilization devices, such as halo vests, are used to immobilize cervical and spinal injuries to facilitate healing. The immobilization devices are normally worn for an extended duration as these sensitive injuries heal. A conventional immobilization device includes front and rear vest components connected to one another and secured to the wearer by a plurality of straps. Halo support rods connect to the vest components and support a halo upright assembly which in turn may be secured to the wearer's head in a variety of known configurations.

While there are numerous known immobilization devices, many of these known devices are inadequate at comfortably distributing pressure exerted onto the chest of the wearer from the halo upright assembly. In particular, many conventional devices apply pressure to anatomical regions which are sensitive to loading. These known devices are cumbersome to apply, particularly for weakened wearers, and do not adequately adapt to the anatomy of the wearer. Moreover, known devices are often found to be ill-fitting and lack means for adjustment to a variety of anatomical sizes.

Accordingly, exemplary embodiments of an immobilization device are described herein which alleviate or eliminate the above-mentioned drawbacks.

SUMMARY

In accordance with an embodiment of the invention, an immobilization device includes an anterior component defining a two-dimensional shaped section contoured to a shape of the human chest. The anterior component forms an anterior outwardly bowed area relative to the two-dimensional shaped anterior section and corresponding to the sternum of the wearer. The device also includes a posterior component defining a two-dimensional shaped section contoured to a shape of the human back. The posterior component forms a posterior outwardly bowed area relative to the two-dimensional shaped section corresponding to the spinal column of the wearer. Elongate cushion elements are connected to and generally confined within a width of the posterior outwardly bowed area. A strapping system connects the anterior and posterior components.

The posterior component defines upper and lower portions. The posterior outwardly bowed portion is preferably three-dimensionally shaped relative to the two-dimensional shaped section forming the remainder of the posterior component.

The posterior component may define an elongate opening extending between the upper and lower portions of the posterior component and generally corresponding to the spinal column of the wearer. It follows that two cushion elements are preferably adhered to the posterior component within the posterior outwardly bowed area and on opposed sides of the opening and generally corresponding to sides of the spinal column of the wearer. The cushion elements may be secured at an upper portion of the posterior component, and extend past the posterior bowed area to the lower portion of the posterior component.

The posterior component may define opposed upper arms each having a living hinge such that the strapping system connects to the upper arms and extends over the living hinges. An upper portion of the posterior component defines a posterior curved recess extending laterally across thereof. The immobilization device further includes a posterior cross plate having dimensions corresponding to the posterior recess and arranged to be secured within the posterior recess. The posterior cross plate is contoured to correspond to the posterior bowed area. The immobilization device further comprises an upright halo support having at least two rods securing to opposed ends of the posterior cross plate.

The anterior component defines an anterior curved recess extending laterally across the anterior component, and further includes an anterior cross plate having corresponding dimensions to the anterior recess and arranged to be secured within the anterior recess. The anterior cross plate is preferably contoured to correspond to the anterior outwardly bowed area. An upright halo support having at least two rods may secure to opposed ends of the anterior cross plate.

A lower strapping system includes first and second strap stabilizers each having a first end connected to corresponding first and second sides, respectively, of a lower portion of the posterior component. First and second slots are formed on the anterior component for loosely receiving a second end of the first and second lower strap stabilizers, respectively. First and second elastic lower straps each having a first end are connected to the first and second lower strap stabilizers at the lower portion of the posterior component, respectively. The lower straps adjustably extend over the first and second lower strap stabilizers and have second ends securable to one another. According to one variation of the strapping system, the second end of each of the lower strap stabilizers is trimmable in length.

The lower strap stabilizers preferably define a retention element near the first end thereof arranged for retaining the lower elastic straps in close proximity therewith on the posterior side of the immobilization device. The lower strap stabilizers may be detachably connected to the posterior component, and the lower strap stabilizers may have greater rigidity than the elastic straps. Furthermore, the second ends of the lower straps can have a plurality of unfixed locations which secure to one another.

The strapping system also includes first and second upper shoulder strap stabilizers each having a first end connected to corresponding first and second sides, respectively, of an upper portion of the posterior component. First and second upper straps each having a first end are connected to the first and second sides of the upper portion of the posterior component, respectively. The upper straps adjustably extend over and beyond the first and second upper strap stabilizers and connect to corresponding first and second sides of an upper portion of the anterior component. The first and second sides of the upper portion of the posterior component each define a living hinge permitting articulation of the upper portion of the posterior upon tensioning of the upper straps.

BRIEF DESCRIPTION OF THE DRAWINGS

Features, aspects, and advantages of the present invention will become better understood with regard to the following description, appended claims, and accompanying drawings.

DETAILED DESCRIPTION OF VARIOUS EMBODIMENTS

A. Overview

Figure 1:
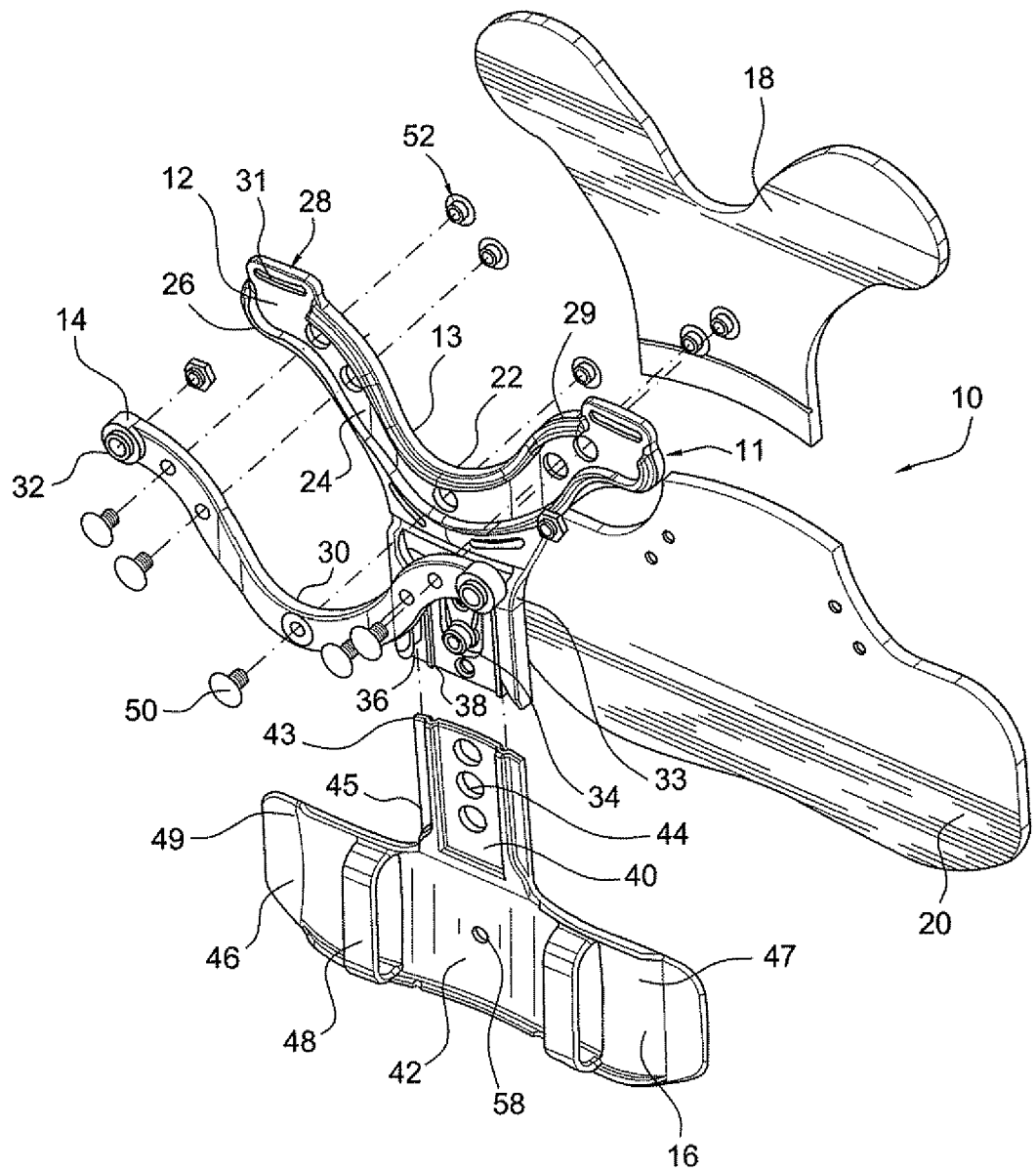
FIG. 1 is an exploded perspective view of an anterior component according to an embodiment of the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Immobilization Device

In general, the immobilization device includes an anterior vest assembly and a posterior vest assembly connecting to the anterior vest assembly via a halo upright assembly and a strapping system. Interface plates form part of the anterior and posterior vest assemblies, and serve as mounting supports for the upright assembly. Suitable padding is provided which corresponds to the anterior and posterior vest assemblies, and secures to rear surfaces thereof and are located adjacent to the body of the wearer.

The anterior and posterior vest assemblies each have a configuration that minimizes pressure on bony prominences of the wearer. Specifically, the contours of the vest assemblies include contoured surfaces at curved bone areas of the wearer, and outwardly bowed areas to minimize pressure at particularly sensitive anatomical regions. Indeed, corresponding vest assemblies cover the sternum but bow outwardly thereat, and partially cover the ribs, but may not directly engage the wearer's shoulder blades, or the spinous processes.

The halo upright is particularly provided to maintain the head of the wearer in a predetermined spatial relationship to the body of the wearer, and includes a plurality of support plates and support rods which couple to the interface plates for securing to the anterior and posterior vest assemblies. An upper strapping system includes adjustable-length flexible straps connecting the vest assemblies at the top or shoulders of the wearer, and a lower strapping system including an adjustable length belt connecting the vest assemblies at the lower portion or the lower chest or abdominal regions of the wearer.

In view of these basic features of the immobilization device, attention is turned to the individual features of the anterior and posterior vest component assemblies.

Figure 2:
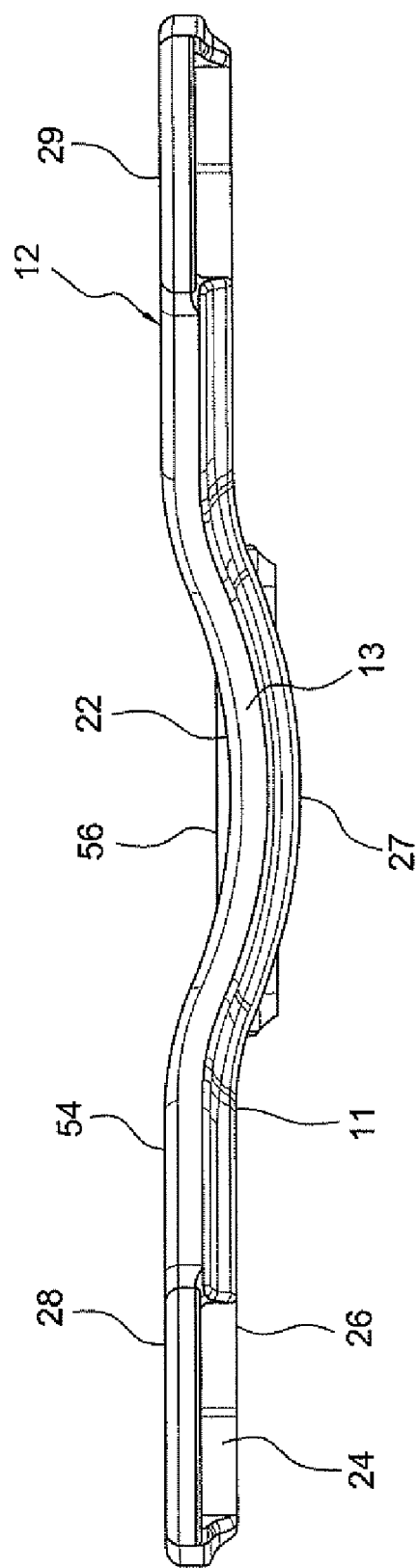
FIG. 2 is a top elevational view showing the anterior top component according to FIG. 1.

An exemplary anterior vest assembly or 10 according to the immobilization device of the present invention is shown by way of FIGS. 1 and 2. The anterior vest assembly 10 includes a top component 11, an interface plate 14 extending laterally across the top component 11, and a bottom component 16 adjustably connected to the top component 11. The top and bottom components 11, 16 may be constructed from a semi-rigid or rigid polymeric material, and may be generally shaped to the contours of a human chest. Padding 18, 20 is provided which lines inner surfaces of the top and bottom components 11, 16, respectively.

The top component 11 has an upper portion 12 including first and second arms 28, 29 separated by a recessed arcuate profile 13 defined therebetween. The region proximate the arcuate profile 13 downwardly extends into the top component 11 and is located between the arms 28, 29 thereby defining a three-dimensionally outwardly bowed portion 22. Thus, where the top component 11 overlies the sternum of the wearer, the bowed portion 22 spaces the top component 11 from the sternum of the wearer. It follows that the top component universally applies or does not apply any pressure to the area at and immediately surrounding the wearer's sternum.

The three-dimensionally shaped bowed portion 22 is contoured markedly different in contrast to the remainder surfaces 54, 56 of the top and bottom components 11, 16 (shown herein by example in a flat configuration), respectively, which may be considered as being two-dimensionally shaped relative to the bowed portion. The two-dimensional shape in other words is defined as adhering to the generically shaped features of the top and bottom components, whereas the bowed portion protrudes outwardly relative to the remainder surfaces.

The top component 11 defines a curvilinear recess 24 which closely conforms to the shape of the anterior interface plate 14, thereby enabling the interface plate 14 to be securely received therein. As depicted in FIG. 1, the curvilinear recess 24 and the interface plate 14 likewise are shaped to correspond to the arcuate profile 13. Indeed, the curvilinear recess 24 is formed over at least a portion of the bowed portion 22, and thereby both the curvilinear recess 24 and the interface plate 14 have bowed portions, 27, 30, respectively, which are shaped to likewise protrude outwardly along with the bowed portion 22 of the upper portion 12 relative to the remainder surfaces of the top component 11. The interface plate 14 is secured to the top component 11 via suitable male and female fasteners 50, 52.

A lip 26 protrudes from the top component 11 and extends along upper and lower perimeters of the curvilinear recess 24 so as to retain the interface plate 14 therein. Moreover, the extent at which the lip 26 protrudes outwardly from the top component 11 is preferably the same distance as the thickness as the interface plate 14. Therefore, the interface plate 14 and the lip 26 are flush with one another, thereby providing a relatively smooth combination of surfaces.

There is an absence or interruption of the lip 26 at the top portion of the first and second arms 28, 29. Instead, a slot 31 is formed from the top component and is used to couple with shoulder straps extending from the posterior vest assembly 100. The absence of the lip at the top portion of the first and second arms 28, 29 also allows for attachment points 32 formed at opposed ends of the interface plate 14 to be exposed for coupling to corresponding support rods of the upright assembly.

The top component 11 includes an elongate attachment portion 33 located at a lower portion thereof. While the attachment portion 33 and the bottom component 16 are connected in a similar manner to the subassembly described in U.S. Pat. No. 6,921,376, incorporated herein by reference, there are a few deviations.

The attachment portion 33 includes an affixation point 34 which is a button biased outwardly which locks onto one of a series affixation points 44 defined on a centrally located strut segment 40 formed by the bottom component 16 to secure the top and bottom components together. The series of affixation points 44 permits adjustment of the height position of the bottom component relative to the top component, thereby accommodating patients of different body types. The attachment portion 33 defines opposed laterally extending flanges directed toward the affixation point 44, and sized so as to slidably receive and retain outer edges 45 of the bottom component 16. The attachment portion 33 also defines elongate ribs 38 that are correspondingly received by channels 43 formed on the bottom component 16.

The bottom component 16 defines lateral wings 46, 47 extending from a central lower region 42. The wings 46, 47 are adapted to extend about at least the anterior regions of the wearer's ribs to thereby bear on selected muscle groups. The wings 46, 47 define loops 48, and the central lower region 42 defines an aperture 50. The loops 48 and the aperture 50 are adapted to receive suitable straps or similar affixation elements that permit the anterior and posterior vest assemblies to be comfortably and securely fitted onto the wearer.

Figure 3:
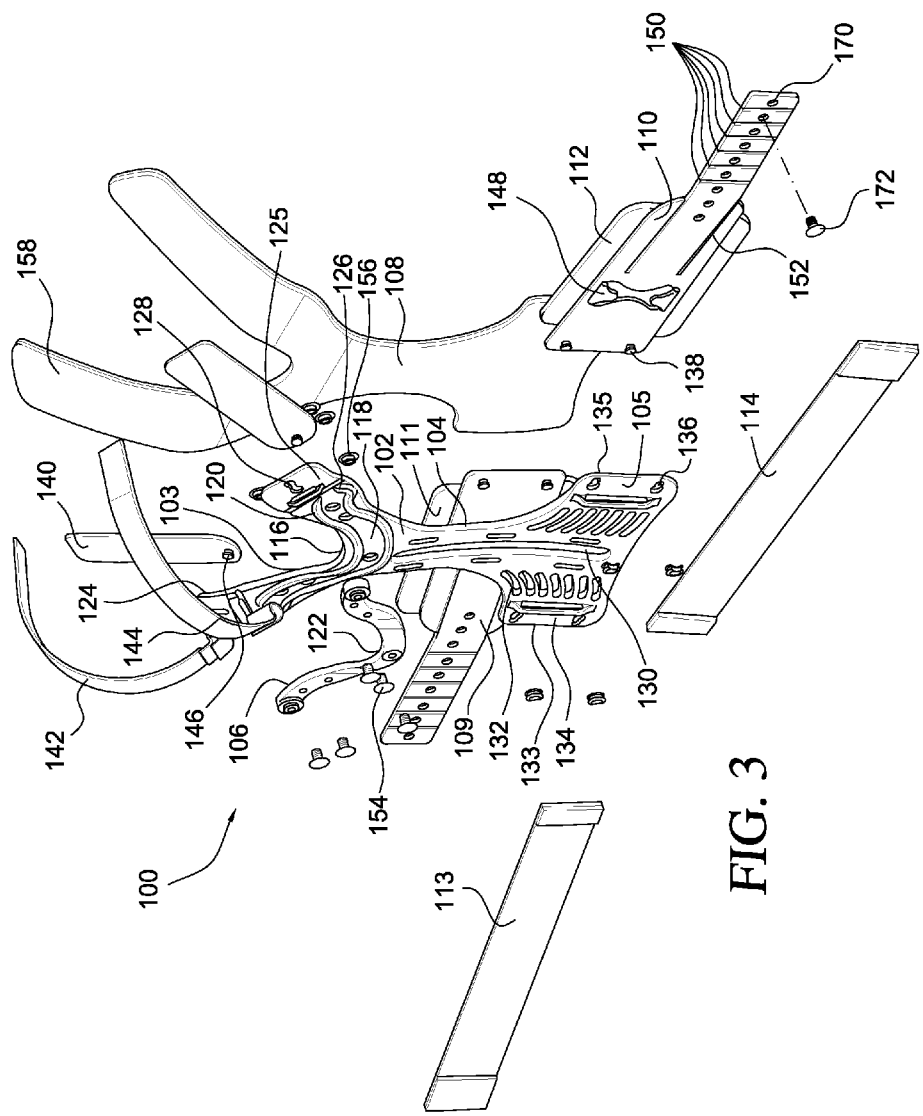
FIG. 3 is an exploded perspective view of a posterior assembly according to an embodiment of the invention.
Figure 4:
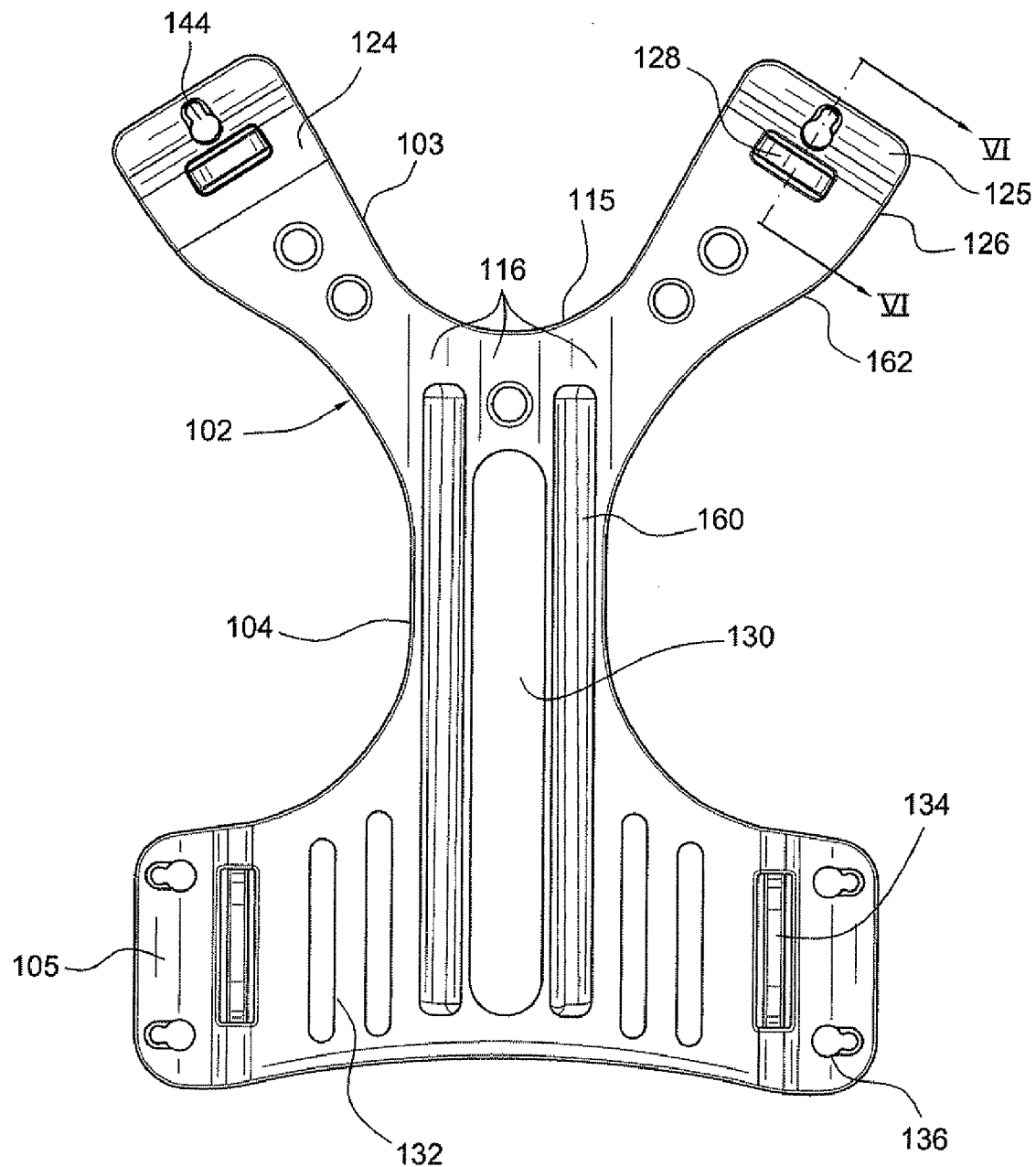
FIG. 4 is an elevational view of a variation of the posterior component according to FIG. 3.
Figure 5:
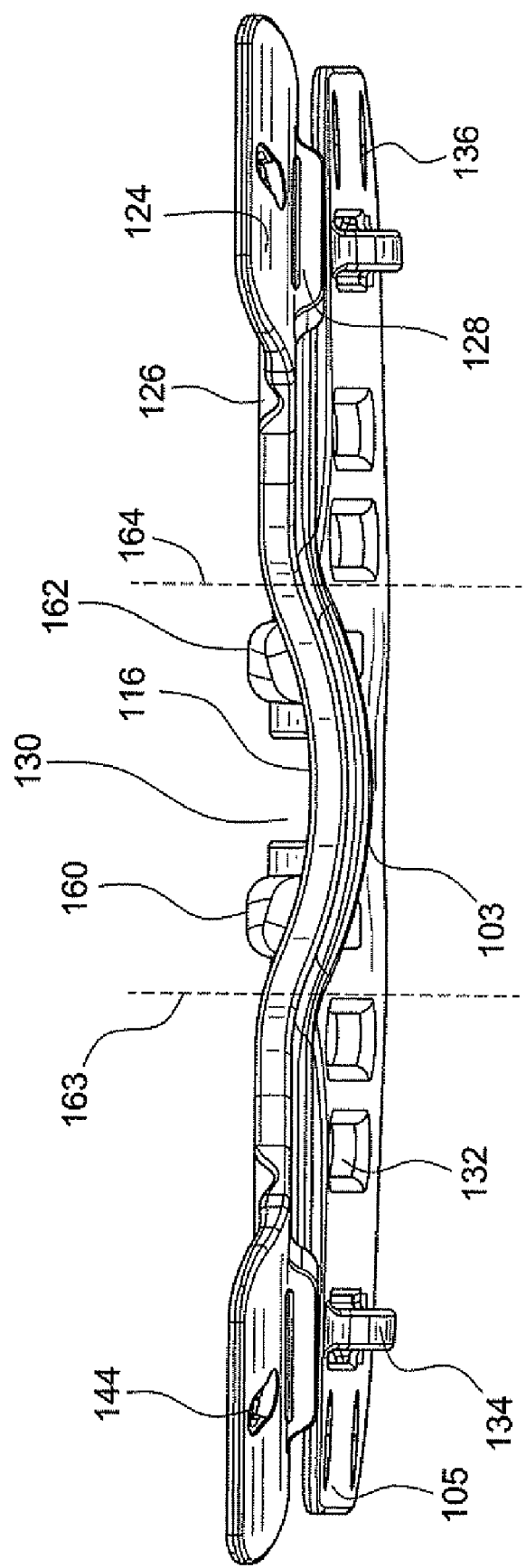
FIG. 5 is a top plan view of the posterior component according to FIG. 4.

Turning to the posterior vest assembly, FIGS. 3-5 depict an embodiment of a posterior vest assembly 100. The posterior vest assembly 100 includes a posterior component 102 having upper, middle and lower portions 103, 104, 105. As with the anterior top component 11, an interface plate 106 secures to the upper portion 103, and provides a means to secure the upright assembly. Likewise, padding 108 is secured to an inner surface of the posterior component 102.

In a similar manner to the anterior top component 11, the posterior component 102 defines an outwardly bowed portion 116 generally confined to the upper portion 103. The outwardly bowed portion 116 is defined generally in a vertical direction along the vertical centerline at the upper portion 103. The posterior component 102 has a generally curved configuration through the upper, middle and lower portions corresponding to a wearer's back. The bowed portion 116 is generally three-dimensional in relation to remainder surfaces or regions comprising the remainder of the posterior component.

Again, in another similarity to the anterior top component, a segment of the periphery of the posterior component 102 at the upper portion 103 defines an arcuate profile 115 and extends downwardly towards the middle portion 104. The upper portion 103 forms wings 124, 125 located on opposed sides of the arcuate profile 115. The wings 124, 125 each define a living hinge 125, loops 128, and locking elements 144 for securing and guiding suitable straps for connecting to the top component of the anterior vest component assembly.

Figure 6:
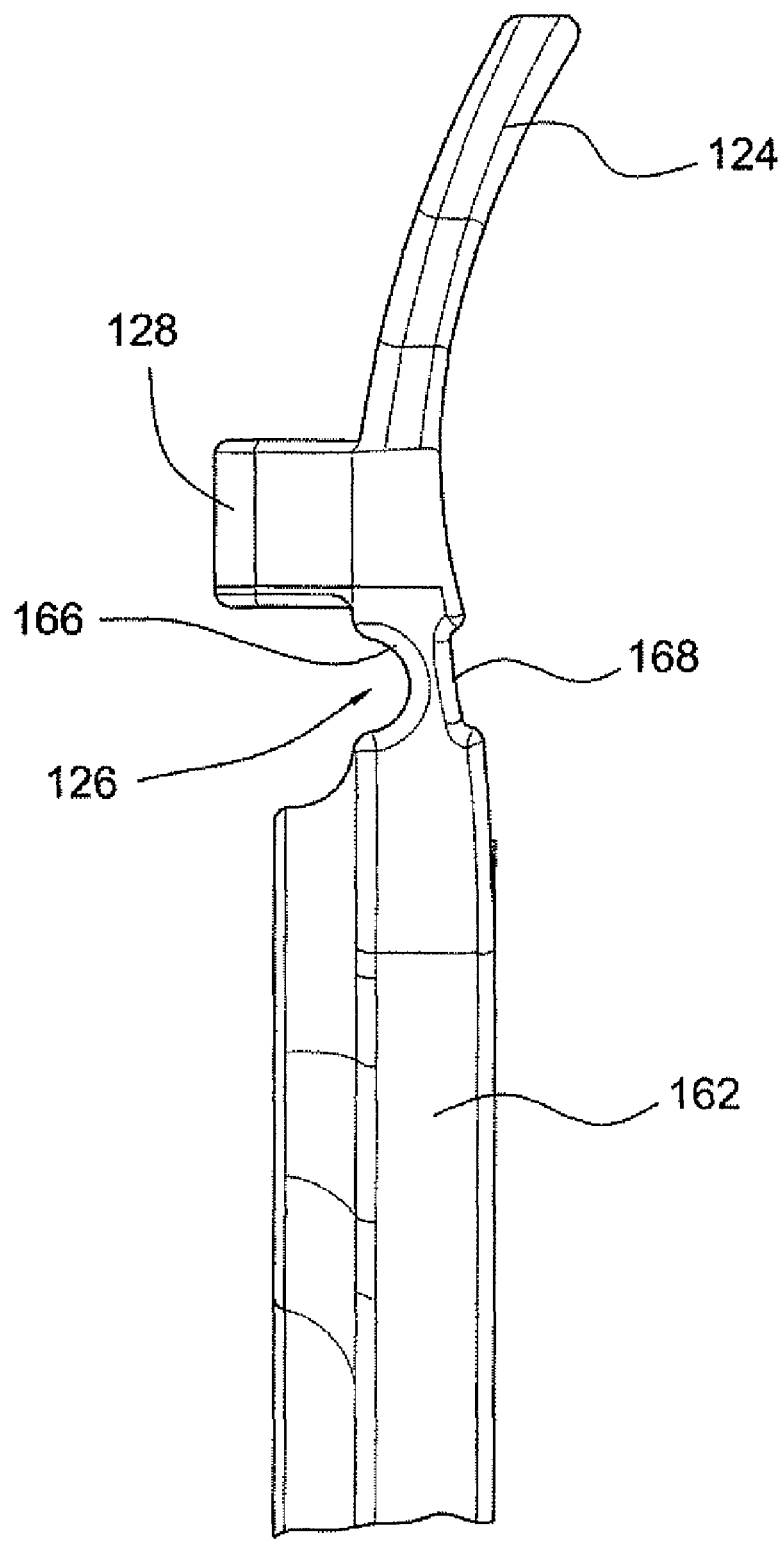
FIG. 6 is a sectional view taken along line VI-VI in FIG. 4.

In reference to FIG. 6, the living hinge 126 includes frontal and rear indentations 166, 168, respectively, which permit the hinge 126 to flex both outwardly and inwardly toward the wearer. The living hinge 126 is particularly advantageous to permit some movement or adjustability of the wings 124, 125 since the posterior component is either rigid or semi-rigid. The flexure of wings 124, 125 provided by the living hinge 126 therefore permits a more conforming fit about the shoulder when the straps connecting to the wings 124, 125 are tensioned. This leads to more secure and comfortable fitting of the immobilization device on the wearer.

The upper portion 103 also defines a curvilinear recess 118 having an outwardly extending lip 120 located along portions of the periphery thereof, and extending between wings 124, 125 formed on opposed sides of the upper portion 103. The interface plate 106 fits securely within the recess 118, and corresponds therewith in shape. Both the interface plate 106 and the recess 118 have outwardly bowed portions 122, 123 which correspond in location and shape to the outwardly bowed portion 116. Suitable fastening elements 154, 156 are used to secure the interface plate 106 to the posterior component 102.

The posterior component 102 defines an elongate opening 130 which is located along the centerline of the posterior component and generally corresponds to the spinal column of a wearer of the immobilization device. In addition, the posterior component 102 forms a plurality of ventilation slots 132 which facilitate circulation of air between the posterior component and the wearer.

The posterior vest assembly 100 includes padding elements 160, 162 extending along the spinal column and generally conforming to the shape of the posterior component. In particular, the padding elements 160, 162 extend at least in part into the outwardly bowed portion 116 located at the upper portion of the posterior component 102. Additionally, the padding elements 160, 162 extend along portions alongside the opening 130.

The padding elements 160, 162 are provided to minimize any pressure that may be exerted against the wearer by the immobilization device along the spinal column of the wearer. Indeed, the padding elements 160, 162 fall within the confines 163, 164 of the outwardly bowed portion 116, so as to provide cushioning within this region, and effectively minimize any pressure loads against the spinal column of the wearer.

Turning to the lower strapping system for securing the posterior vest assembly 100 to the anterior vest assembly 10, the lower portion 105 of the posterior component 102 defines lower lateral wings 133, 135 protruding outwardly relative to the centerline of the posterior component. The lower strapping system also includes bendable strap stabilizers 109, 110 having locking elements 138 and connect to locking slots or keyholes 136 formed on the lateral wings 133, 135. The lower strapping system further includes elastic straps 113, 114 that secure to belt loops 134 formed on the lateral wings 133, 135, and overlie on an outer surface of the strap stabilizers 109, 110. Suitable padding 112 is connected to an inner surface of the strap stabilizers 113, 114 and adjacently faces the wearer.

The strap stabilizers 109, 110 are more rigid and have a greater height than the elastic straps 113, 114. The height of the strap stabilizers 109, 110 provides a greater coverage over the wearer than the elastic straps 113, 114. This configuration allows for improved distribution of pressure about the wearer, and a more stable support about the wearer. The strap stabilizers define retention elements 148 which maintain the elastic straps 113, 114 over the strap stabilizers 113, 114, assure that they do not drift over areas of the wearer that are not covered by the strap stabilizers 113, 114.

Figure 7:
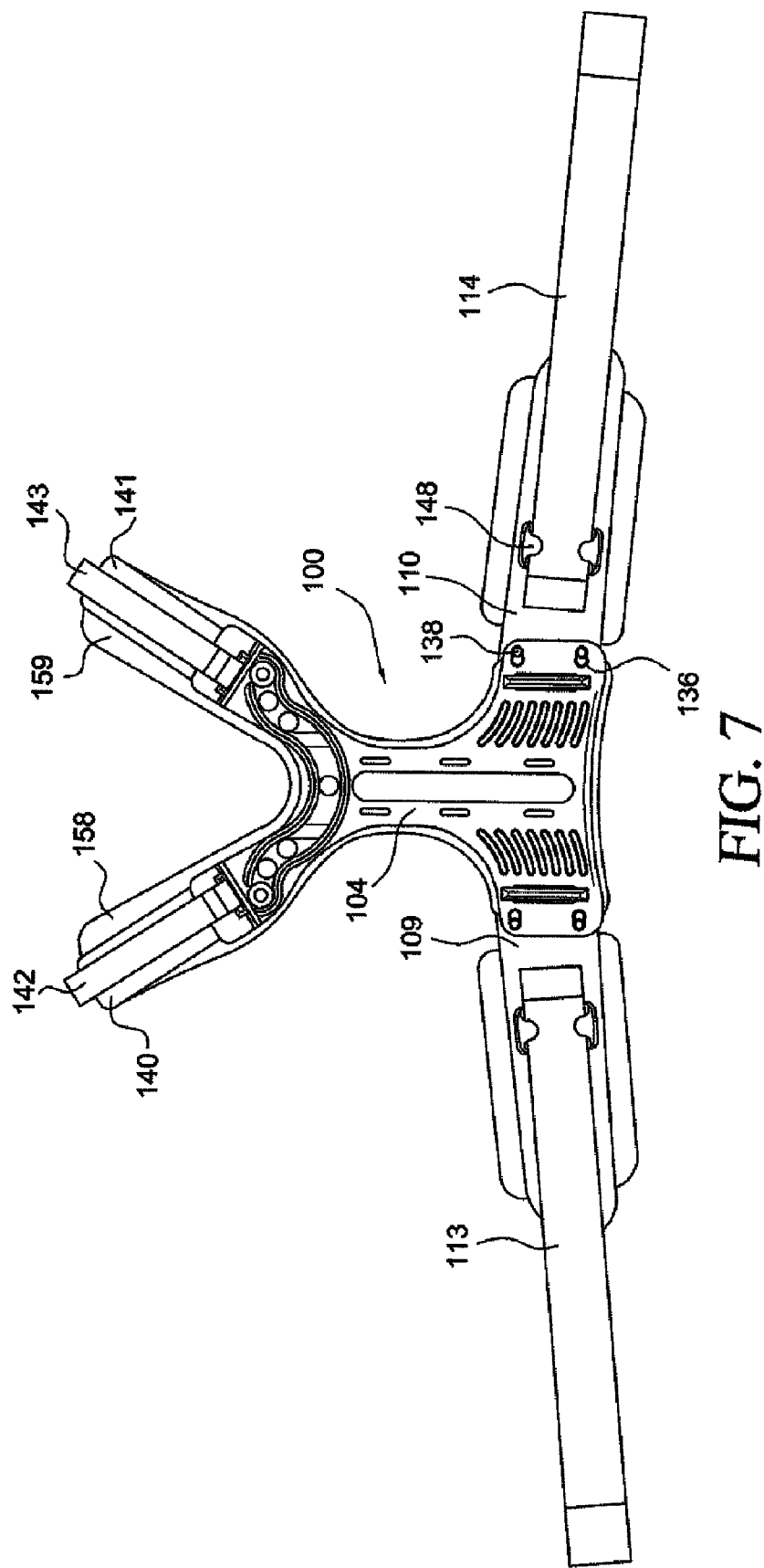
FIG. 7 is schematic view of the posterior vest assembly according to FIG. 3.

In referring to FIG. 7, the strap stabilizers 109, 110 are connected to the posterior component 104. The strap stabilizers 109, 110, and elastic straps 113, 114 are arranged to extend about the wearer and through the belt loops 48 on the anterior component 11.

According to one variation, the strap stabilizers 109, 110 each define a plurality of apertures 170 which may be fixably secured via an affixation element 172 which couples an aperture 170 on both strap stabilizers 109, 110 to the affixation point 58 located on the anterior component 11. Alternatively, the strap stabilizers 109, 110 extend through the belt loops 48 on the anterior component 11 without any particular and direct affixation to the anterior component 11. Instead, the elastic straps 113, 114 connect to one another (via, for example, hook and loop fasteners) and secure the strap stabilizers 109, 110 via pressure exerted thereover. This variation provides for a more flexible fit, and allows for an ease of attachment of the immobilization device onto the wearer.

In addition to the aforementioned features of the strap stabilizers, the strap stabilizers 109, 110 define trim lines 150 at selected locations which permit the sizing of the strap stabilizers to the girth of the wearer. Also, each strap stabilizer 109, 110 defines separation lines 152 which allow for portions of the strap stabilizers corresponding to the elastic straps to better conform to wearer when the elastic straps are tensioned. The separation lines 152 have the particular advantage of enabling a base portion of the strap stabilizers connecting to the posterior component to remain more rigid and/or robust, which portions of the strap stabilizers corresponding to the elastic straps with greater flexibility.

The upper strapping system also includes sections particularly arranged for securing the posterior vest assembly to the anterior vest assembly over the wearer's shoulders. Specifically, the upper strapping system includes strap stabilizers 140, 141 that attach to the wings 124, 125 in a similar manner as do the strap stabilizers 109, 110 to the lateral wings 133, 135. Further, straps 142, 143 overlie an outer surface of the strap stabilizers 140, 141 in a similar manner as do the elastic straps 113, 114 over the strap stabilizers 109, 110. The straps 142, 143 couple to corresponding loops 31 of the anterior component 11. However, the strap stabilizers 140, 141 may extend only over part of the shoulder of the wearer or completely over the shoulder of the wearer and secure to the loops 31 on the anterior component 11. Suitable padding 158, 159 underlie the inner surface of the strap stabilizers 140, 141 so as to provide additional comfort to the wearer.

Figure 8:
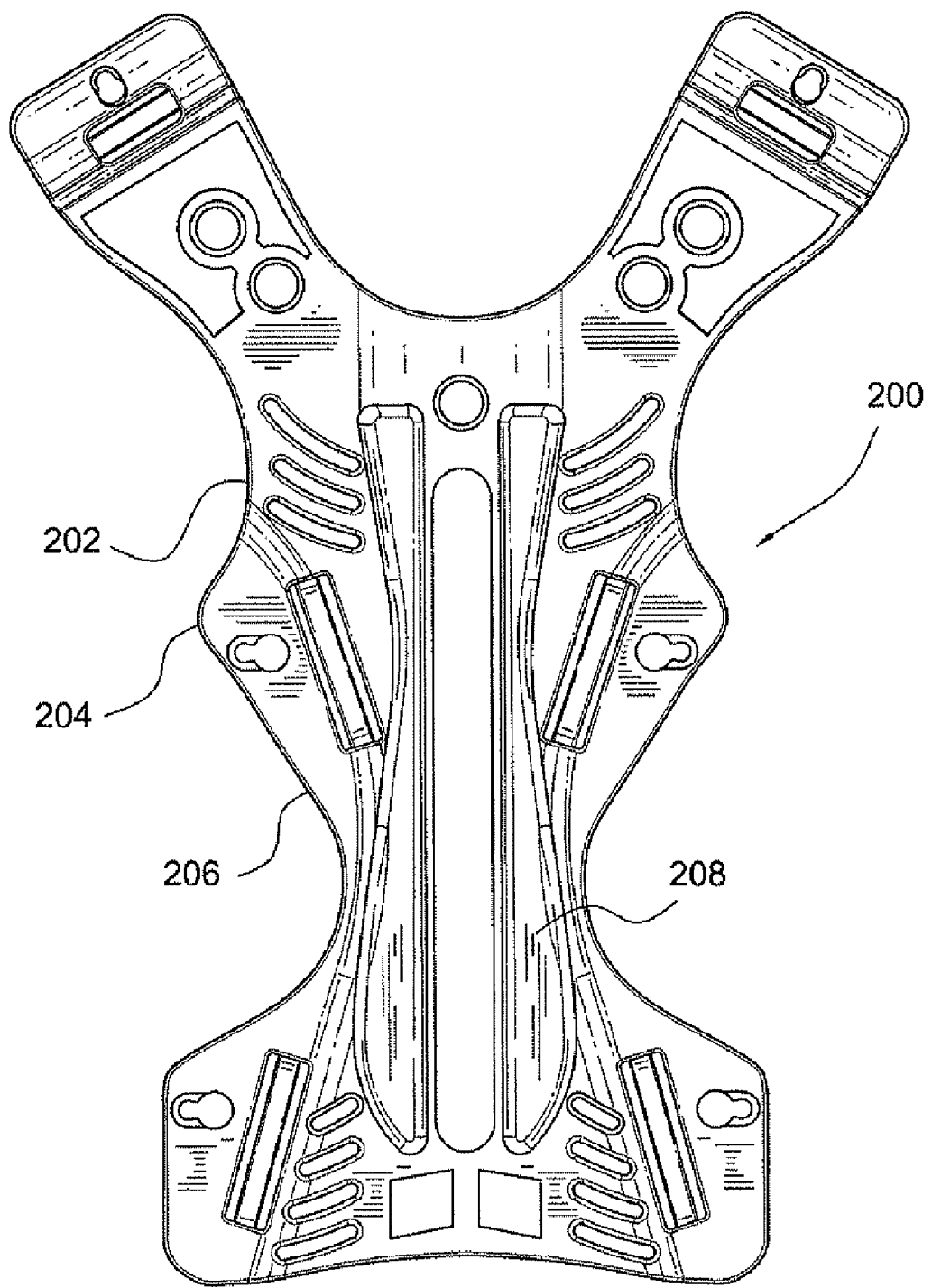
FIG. 8 is an elevational view of another variation of the posterior component.

In referring to FIG. 8, another variation of the posterior component 200 is depicted. This variation of the posterior component 200 is particularly designed to accommodate a wearer having a longer back. The posterior component 200 includes many of the same features as the posterior component 102. However, this posterior component 200 includes vertically curved contours on the side periphery thereof including sections 202, 206 located between laterally protruding section 204. Additionally, elongate pads 208 are secured to the inner surface of posterior component 200 and generally correspond to the geometry thereof.

While the foregoing embodiments have been described and shown, it is understood that alternatives and modifications of these embodiments, such as those suggested by others, may be made to fall within the scope of the invention.

The invention claimed is:

1. An immobilization device, comprising:
   an anterior component including a two-dimensional shaped section contoured to a shape of the human chest, the anterior component forming an anterior outwardly bowed area relative to the two-dimensional shaped anterior section and corresponding to the sternum of the wearer, an upper portion of the anterior component defines an anterior curved recess extending laterally across thereof;
   an anterior cross plate arranged to be secured within the anterior recess;
   a posterior component including a two-dimensional shaped section contoured to a shape of the human back, the posterior component forming a posterior outwardly bowed area relative to the two-dimensional shaped section corresponding to the spinal column of the wearer, an upper portion of the posterior component defines a posterior curved recess extending laterally across thereof;
   a posterior cross plate arranged to be secured within the posterior recess;
   a strapping system connecting the anterior and posterior components.

2. The immobilization device according to claim 1, wherein the anterior cross plate is contoured to correspond to the anterior outwardly bowed area.

3. The immobilization device according to claim 1, further comprising an upright halo support having at least two rods securing to opposed ends of the anterior cross plate.

4. The immobilization device according to claim 1, wherein the posterior cross plate is contoured to correspond to the posterior bowed area.

5. The immobilization device according to claim 1, further comprising an upright halo support having at least two rods secured to opposed ends of the posterior cross plate.

6. An immobilization device, comprising:
   an anterior component including a two-dimensional shaped section contoured to a shape of the human chest, the anterior component forming an anterior outwardly bowed area relative to the two-dimensional shaped anterior section and corresponding to the sternum of the wearer, an upper portion of the anterior component defines an anterior curved recess extending laterally across thereof;
   an anterior cross plate arranged to be secured within the anterior recess;
   a posterior component including a two-dimensional shaped section contoured to a shape of the human back, the posterior component forming a posterior outwardly bowed area relative to the two-dimensional shaped section corresponding to the spinal column of the wearer, an upper portion of the posterior component defines a posterior curved recess extending laterally across thereof;
   a posterior cross plate arranged to be secured within the posterior recess;
   a strapping system connecting the anterior and posterior components;
   wherein the posterior component defines at least one living hinge, the strapping system connecting to the living hinge, the living hinge having frontal and rear indentations arranged to permit the living hinge to flex in both outwardly and inwardly directions.

* * * * *